(12) United States Patent
Hsu et al.

(10) Patent No.: US 11,744,542 B2
(45) Date of Patent: Sep. 5, 2023

(54) METHOD FOR EVALUATING MOVEMENT STATE OF HEART

(71) Applicant: Acer Incorporated, New Taipei (TW)

(72) Inventors: Hung-Sheng Hsu, New Taipei (TW); Chien-Hung Li, New Taipei (TW); Yi-Jin Huang, New Taipei (TW)

(73) Assignee: Acer Incorporated, New Taipei (TW)

(*) Notice: Subject to any disclaimer, the term of this patent is extended or adjusted under 35 U.S.C. 154(b) by 170 days.

(21) Appl. No.: 17/233,566

(22) Filed: Apr. 19, 2021

(65) Prior Publication Data

US 2022/0296210 A1  Sep. 22, 2022

(30) Foreign Application Priority Data

Mar. 17, 2021  (TW) .................................. 110109633

(51) Int. Cl.
*A61B 8/08* (2006.01)
*A61B 8/00* (2006.01)
*G06T 7/00* (2017.01)

(52) U.S. Cl.
CPC ............ *A61B 8/0883* (2013.01); *A61B 8/466* (2013.01); *G06T 7/0012* (2013.01);
(Continued)

(58) Field of Classification Search
CPC ......... A61B 8/0883; A61B 8/466; A61B 8/02; A61B 8/5223; G06T 7/0012;
(Continued)

(56) References Cited

U.S. PATENT DOCUMENTS

| 5,322,067 A | 6/1994 | Prater et al. |
| 2002/0123688 A1* | 9/2002 | Yamauchi ............ A61B 8/0883 |
| | | 600/443 |

(Continued)

FOREIGN PATENT DOCUMENTS

| CN | 100403989 | 7/2008 |
| CN | 109690554 | 4/2019 |

(Continued)

OTHER PUBLICATIONS

Carol Mitchell et al., "Guidelines for Performing a Comprehensive Transthoracic Echocardiographic Examination in Adults: Recommendations from the American Society of Echocardiography", Journal of the American Society of Echocardiography, vol. 32, Issue 1, Jan. 2019, pp. 1-64.

(Continued)

*Primary Examiner* — Yi-Shan Yang
*Assistant Examiner* — Alexei Bykhovski
(74) *Attorney, Agent, or Firm* — JCIPRNET

(57) ABSTRACT

A method for evaluating a movement state of a heart is provided and includes: obtaining a plurality of consecutive heart ultrasound images corresponding to a heart and accordingly estimating a plurality of left ventricular volumes corresponding to the heart ultrasound images; finding a plurality of specific extremums in the left ventricular volumes and accordingly estimating a plurality of time differences among the specific extremums; estimating a statistical characteristic value of the time differences based on the time differences; and determining that an abnormal movement state of the heart occurs in response to determining that at least one of the time differences deviates from the statistical characteristic value up to a predetermined threshold.

8 Claims, 5 Drawing Sheets

(52) U.S. Cl.
CPC ............... *G06T 2207/10132* (2013.01); *G06T 2207/20081* (2013.01); *G06T 2207/20084* (2013.01); *G06T 2207/30048* (2013.01)

(58) Field of Classification Search
CPC . G06T 2207/10132; G06T 2207/20081; G06T 2207/20084; G06T 2207/30048; G16H 30/20; G16H 30/40; G16H 50/20; G16H 50/70
See application file for complete search history.

(56) References Cited

U.S. PATENT DOCUMENTS

| | | | | |
|---|---|---|---|---|
| 2012/0078097 | A1* | 3/2012 | Wang .................. | A61B 8/0883 |
| | | | | 600/437 |
| 2015/0071492 | A1* | 3/2015 | Barr ......................... | G06T 7/20 |
| | | | | 382/103 |
| 2018/0106897 | A1* | 4/2018 | Shouldice ............ | A61B 5/0205 |
| 2019/0343482 | A1 | 11/2019 | Abe | |
| 2021/0353166 | A1* | 11/2021 | Sirendi ................ | A61B 5/0816 |

FOREIGN PATENT DOCUMENTS

| | | |
|---|---|---|
| CN | 110664435 | 1/2020 |
| TW | 202022713 | 6/2020 |

OTHER PUBLICATIONS

"Search Report of Europe Counterpart Application", dated Nov. 12, 2021, p. 1-p. 9.

\* cited by examiner

METHOD FOR EVALUATING MOVEMENT STATE OF HEART

CROSS-REFERENCE TO RELATED APPLICATION

This application claims the priority benefit of Taiwan application serial no. 110109633, filed on Mar. 17, 2021. The entirety of the above-mentioned patent application is hereby incorporated by reference herein and made a part of this specification.

BACKGROUND

Technical Field

The disclosure relates to a method for evaluating a medical image, and in particular, to a method for evaluating a movement state of a heart.

Description of Related Art

At present, the most widely used and most economical method for examining the structure of the heart is the heart ultrasound method. When the heart of a patient is required to be examined through ultrasound, the ultrasound technician or doctor generally performs heart scanning by holding an ultrasound probe at a specific angle to check whether the patient's heart structure is abnormal.

In clinical practice, various ways for assessing whether the heart is in good condition are available, and one of these is to measure the left ventricular ejection fraction (LVEF). LEVE measures how much blood is ejected from the left ventricle in each heartbeat. In hospitals, manual inspection or semi-automatic methods are still used to identify the end diastole and end systole (ES) of the heart in the heart rate cycle. After identifying the ED and ES, the built-in tool program of the ultrasound machine can calculate the end-diastolic volume (EDV) and the end-systolic volume (ESV) and then calculates the ejection fraction (EF).

In the current technical field, the AI deep learning model has gradually been used to identify the end diastole and the end systole of the heart in the heart rate cycle, and the tedious work of manually identifying whether the image is ED or ES is thereby lowered.

Nevertheless, in actual clinical situations, the AI deep learning model has not yet replaced manual identification for two reasons. Firstly, when the patient has a heart disease, such as arrhythmia caused by atrial fibrillation, the AI deep learning model will not be able to effectively identify ED and ES, resulting in incorrect calculation of EF. Secondly, when the ultrasound image of the heart obtained by the ultrasound probe is not clear enough, the AI deep learning model will not be able to judge well, and it will not be able to effectively identify ED and ES, resulting in incorrect calculation of EF.

Therefore, for a person having ordinary skill in the art, a mechanism that can be designed to determine whether an abnormal movement state of the heart (such as arrhythmia) of a patient occurs may facilitate effective identification of the end diastole and the end systole of the heart in the heart rate cycle performed by the above-mentioned AI deep learning model, and a correct EF may thus be obtained.

SUMMARY

Accordingly, the disclosure provides a method for evaluating a movement state of a heart, which may be used to solve the foregoing technical problems.

The disclosure provides a method for evaluating a movement state of a heart suitable for an electronic apparatus, and the method includes the following steps. A plurality of consecutive heart ultrasound images corresponding to a heart is obtained, and a plurality of left ventricular volumes corresponding to the heart ultrasound images are accordingly estimated. A plurality of specific extremums in the left ventricular volumes are found, and a plurality of time differences among the specific extremums are accordingly estimated. A statistical characteristic value of the time differences is estimated based on the time differences. An abnormal movement state of the heart is determined to occur in response to determining that at least one of the time differences deviates from the statistical characteristic value up to a predetermined threshold.

To make the aforementioned more comprehensible, several embodiments accompanied with drawings are described in detail as follows.

BRIEF DESCRIPTION OF THE DRAWINGS

The accompanying drawings are included to provide a further understanding of the disclosure, and are incorporated in and constitute a part of this specification. The drawings illustrate exemplary embodiments of the disclosure and, together with the description, serve to explain the principles of the disclosure.

DESCRIPTION OF THE EMBODIMENTS

Figure 1:
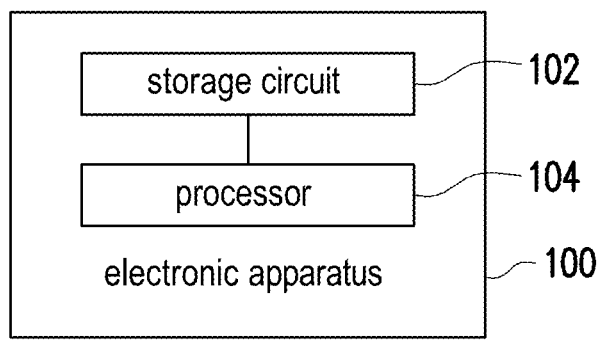
FIG. 1 is a schematic view illustrating an electronic apparatus according to an embodiment of the disclosure.

With reference to FIG. 1, which is a schematic view illustrating an electronic apparatus according to an embodiment of the disclosure. In different embodiments, an electronic apparatus 100 is, but not limited to, a computer apparatus of any type, a smart apparatus, and/or a handheld apparatus, for example.

As shown in FIG. 1, the electronic apparatus 100 includes a storage circuit 102 and a processor 104. The storage circuit 102 is a fixed or a movable random access memory (RAM) in any form, a read-only memory (ROM), a flash memory, a hard disc, other similar devices, or a combination of the foregoing devices, for example, and may be used to record a plurality of program codes or modules.

The processor 104 is coupled to the storage circuit 102 and may be a processor for general use, a processor for special use, a traditional processor, a digital signal processor, a plurality of microprocessors, one or a plurality of microprocessors combined with a digital signal processor core, a controller, a microcontroller, an application specific integrated circuit (ASIC), a field programmable gate array (FPGA) circuit, an integrated circuit of any other types, a state machine, a processor based on an advanced RISC machine (ARM), and the like.

In the embodiments of the disclosure, the processor 104 may access the modules and program codes in the storage circuit 102 to implement a method for estimating a ventricular volume provided by the disclosure, and detailed description is provided as follows.

Figure 2:
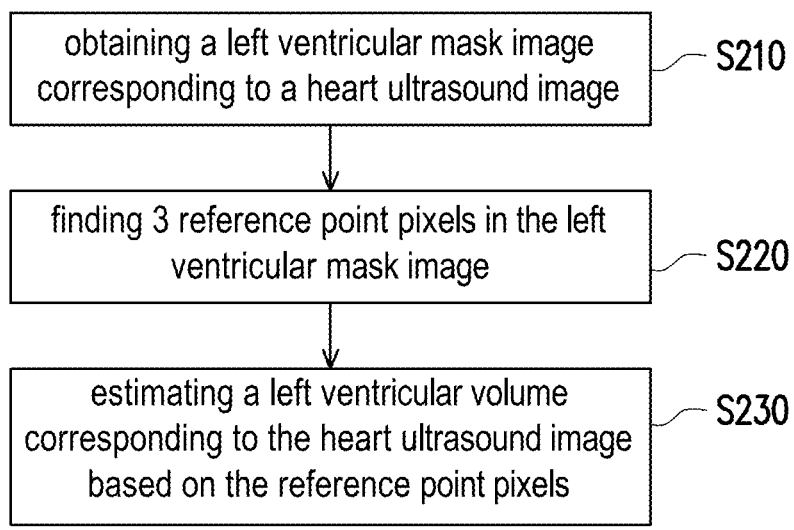
FIG. 2 is a flow chart illustrating a method for estimating a ventricular volume according to an embodiment of the disclosure.
Figure 3:
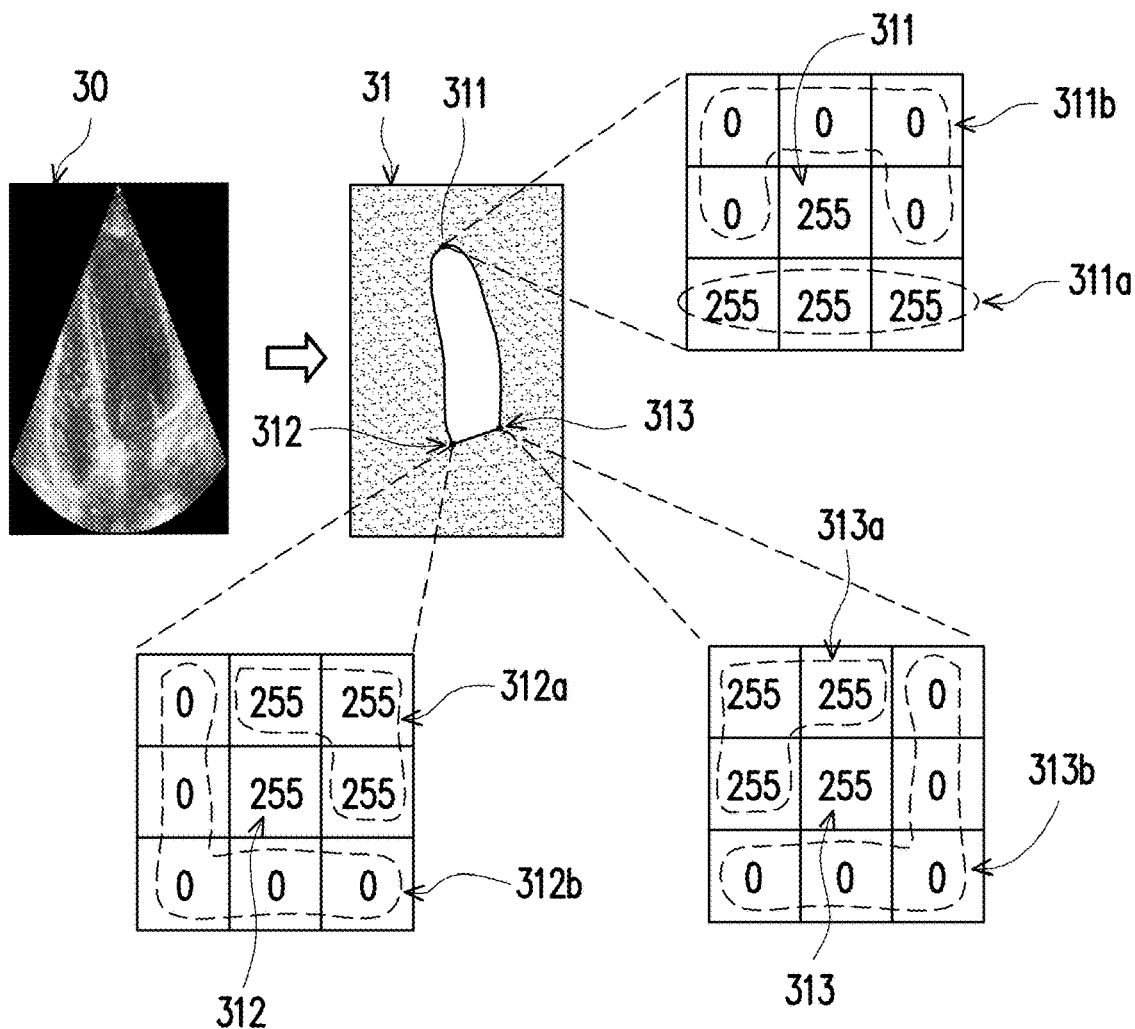
FIG. 3 is a view illustrating an application scenario according to an embodiment of the disclosure.

With reference to FIG. 2 and FIG. 3, FIG. 2 is a flow chart illustrating a method for estimating a ventricular volume according to an embodiment of the disclosure, and FIG. 3 is a view illustrating an application scenario according to an embodiment of the disclosure. The method provided by this embodiment may be implemented by the electronic apparatus 100 of FIG. 1, and details of the steps in FIG. 2 are described as follow in accompanying with the devices shown in FIG. 1 and the scenario of FIG. 3.

First, in step S210, the processor 104 may obtain a left ventricular mask image 31 corresponding to a heart ultrasound image 30, and the left ventricular mask image 31 is a binary image. In the embodiments of the disclosure, the processor 104 may, for example, input an apical view of the heart ultrasound image 30 (e.g., an apical two chamber (A2C) view or an apical four chamber (4C) view) into a pre-trained machine learning model, and the corresponding binary image outputted by this machine learning model corresponding to the heart ultrasound image 30 acts as the left ventricular mask image 31.

In an embodiment, in order to enable the machine learning model to be equipped with the above capabilities, a designer may input various heart ultrasound images of an image region marked with the ventricle as training data into the machine learning model during training of the machine learning model. In this way, the machine learning model may learn characteristics of the image region corresponding to the ventricle and may thus further identify the image region corresponding to the ventricle when an unknown heart ultrasound image is obtained. After that, the machine learning model may, but not limited to, set all pixels in the image region corresponding to the ventricle to a first value (e.g., 255) and set all pixels in the image region not corresponding to the ventricle to a second value (e.g., 0) to generate a corresponding binary image.

After that, in step S220, the processor 104 may find 3 reference point pixels 311 to 313 in the left ventricular mask image 31.

In the embodiments of the disclosure, each of the reference point pixels 311 to 313 may have the first value (e.g., 255). Besides, each of the reference point pixels 311 to 313 may be surrounded by N (e.g., 8) surrounding pixels, and the surrounding pixels of each of the reference point pixels 311 to 313 may include N1 (e.g., 3) first surrounding pixels with the first value and (e.g., 5) second surrounding pixels with the second value (e.g., 0), where N, N1, and N2 are positive integers.

In an embodiment, among the surrounding pixels of the reference point pixel 311, the first surrounding pixels (i.e., the pixels located in a range 311a) are arranged in a straight line, and the second surrounding pixels (i.e., the pixels located in a range 311b) are arranged in a C shape.

In an embodiment, among the surrounding pixels of the reference point pixel 312, the first surrounding pixels (i.e., the pixels located in a range 312a) are arranged in an L shape, and the second surrounding pixels (i.e., the pixels located in a range 312b) are arranged in an L shape.

In an embodiment, among the surrounding pixels of the reference point pixel 313, the first surrounding pixels (i.e., the pixels located in a range 313a) are arranged in an L shape, and the second surrounding pixels (i.e., the pixels located in a range 313b) are arranged in an L shape.

In the embodiments of the disclosure, the reference point pixels 311 to 313 are all unique in the left ventricular mask image 31, so the processor 104 may view each pixel in the left ventricular mask image 31 one by one and define 3 pixels that meet the above conditions (e.g., the pixel having 8 surrounding pixels including 3 first surrounding pixels with the first value and 5 second surrounding pixels with the second value and having the first value) as the reference point pixels 311 to 313.

Next, in step S230, the processor 104 may estimate a left ventricular volume corresponding to the heart ultrasound image 30 based on the reference point pixels 311 to 313. In an embodiment, the processor 104 may estimate distances among the reference point pixels 311 to 313 and accordingly find a first reference point pixel, a second reference point pixel, and a third reference point pixel corresponding to an apex, a first flap of a mitral valve (e.g., left flap of the mitral valve), and a second flap of the mitral valve (e.g., right flap of the mitral valve) respectively among the reference point pixels 311 to 313. Next, the processor 104 may apply a Simpson's rule to estimate the left ventricular volume corresponding to the heart ultrasound image 30 based on the first reference point pixel, the second reference point pixel, and the third reference point pixel.

Figure 4:
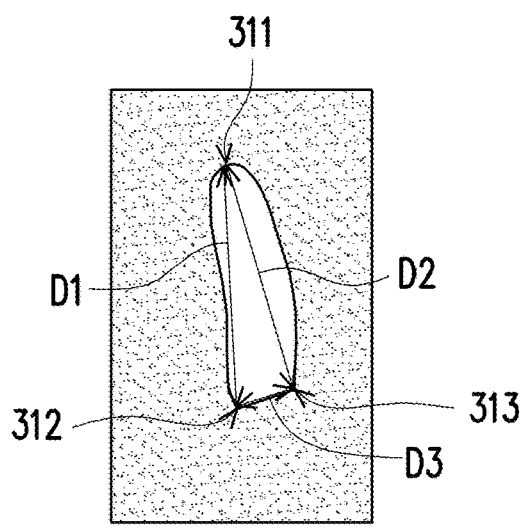
FIG. 4 is a schematic view illustrating finding of a first, second, and third reference point pixels based on distances among the reference point pixels according to an embodiment of the disclosure.

With reference to FIG. 4, which is a schematic view illustrating finding of a first, second, and third reference point pixels based on distances among the reference point pixels according to an embodiment of the disclosure. Generally, a distance between the left flap and the right flap of the mitral valve is less than a distance between the apex and any one of the two flaps of the mitral valve. Therefore, based on this principle, the processor 104 may find the first, second, and third reference point pixels corresponding to the apex, the first flap of the mitral valve, and the second flap of the mitral valve respectively among the reference point pixels 311 to 313.

In FIG. 4, a first distance D1 may be provided between the reference point pixel 311 and the reference point pixel 312, a second distance D2 may be provided between the reference point pixel 311 and the reference point pixel 313, and a third distance D3 may be provided between the reference point pixel 312 and the reference point pixel 313.

In the scenario shown in FIG. 4, in response to determining that the first distance D1 and the second distance D2 are both greater than the third distance D3, the processor may respectively define the reference point pixels 311 to 313 as the first, second, and third reference point pixels.

In another embodiment, in response to determining that the second distance D2 and the third distance D3 are both greater than the first distance D1, the processor 104 may respectively define the reference point pixel 313, the reference point pixel 311, and the reference point pixel 312 as the first, second, and third reference point pixels. Further, in still another embodiment, in response to determining that the first distance D1 and the third distance D3 are both greater than the second distance D2, the processor 103 may respectively define the reference point pixel 312, the reference point pixel 311, and the reference point pixel 313 as the first, second, and third reference point pixels.

In addition, if the heart ultrasound image 30 is determined to be the apical view, among the 3 found reference point pixels, the one with a highest height should correspond to the apex. Therefore, in FIG. 4, the processor 104 may directly define the reference point pixel 311 with the highest height as the first reference point pixel corresponding to the apex and respectively define the remaining reference point pixels 312 and 313 as the second and third reference point pixels corresponding to the mitral valve, which should however not be construed as limitations to the disclosure.

Next, the processor 104 may apply the Simpson's rule to estimate the left ventricular volume corresponding to the heart ultrasound image 30 based on the first, second, and third reference point pixels, and description details thereof may be found with reference to documents of the related art and are not repeated herein.

Figure 5A:
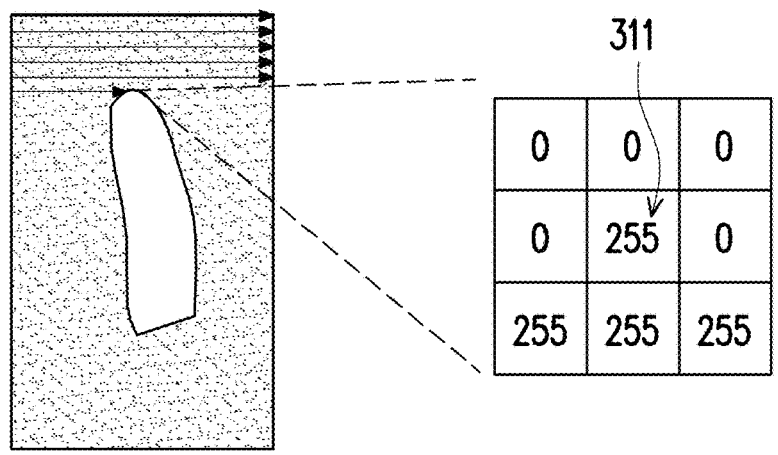
FIG. 5A is a schematic view illustrating finding of a reference point pixel corresponding to an apex according to FIG. 3.
Figure 5B:
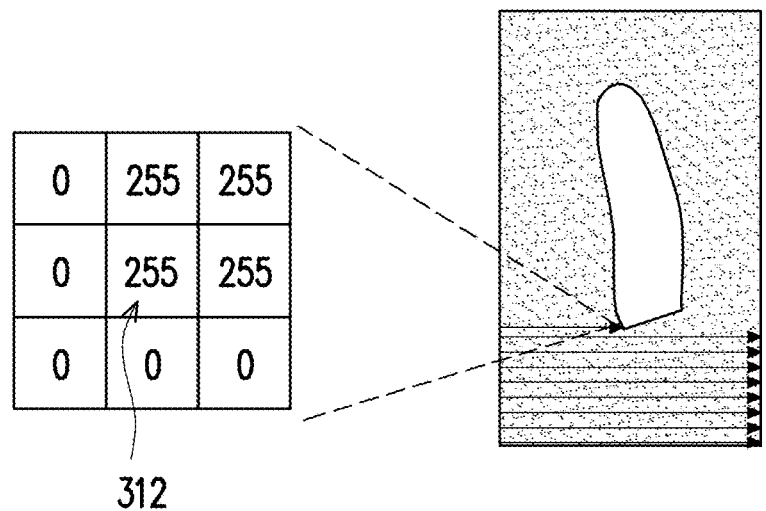
FIG. 5B is a schematic view illustrating finding of a reference point pixel corresponding to a left flap of a mitral valve according to FIG. 5A.
Figure 5C:
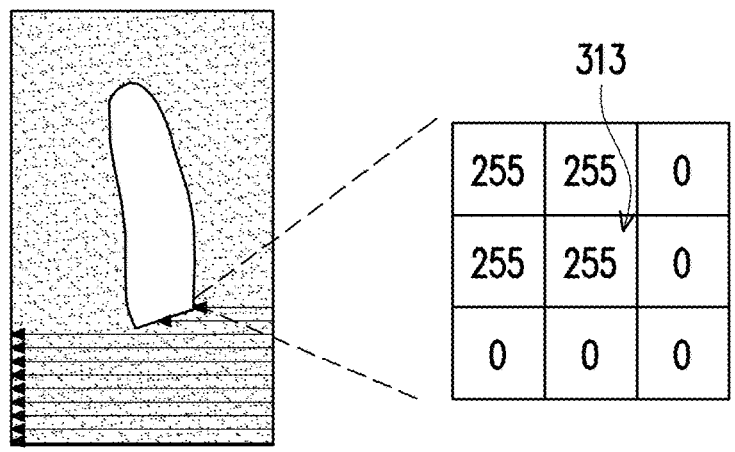
FIG. 5C is a schematic view illustrating finding of a reference point pixel corresponding to a right flap of the mitral valve according to FIG. 5B.

Besides, in order to improve efficiency of finding the reference point pixels 311 to 313, the processor 104 may further find the reference point pixels 311 to 313 based on mechanisms shown in FIGS. 5A to 5C.

With reference to FIG. 5A, which is a schematic view illustrating finding of a reference point pixel corresponding to an apex according to FIG. 3. As described above, if the heart ultrasound image 30 is determined to be the apical view, among the 3 found reference point pixels, the one with the highest height should correspond to the apex.

Accordingly, starting from a highest pixel row in the left ventricular mask image 31, the processor 104 may scan down row by row to find the pixel satisfying the above conditions (e.g., the pixel having 8 surrounding pixels including 3 first surrounding pixels with the first value and 5 second surrounding pixels with the second value and having the first value). In FIG. 5A, when one pixel satisfying the above conditions is found, the processor 104 may directly define this pixel as the reference point pixel 311 corresponding to the apex and stop scanning.

With reference to FIG. 5B, which is a schematic view illustrating finding of a reference point pixel corresponding to a left flap of a mitral valve according to FIG. 5A. In the case that the heart ultrasound image 30 is determined to be the apical view, among the 3 found reference point pixels, the lower left one should correspond to the left flap of the mitral valve.

Accordingly, starting from a lowest pixel row in the left ventricular mask image 31, the processor 104 may scan from left to right row by row to find the pixel satisfying the above conditions (e.g., the pixel having 8 surrounding pixels including 3 first surrounding pixels with the first value and 5 second surrounding pixels with the second value and having the first value). In FIG. 5B, when one pixel satisfying the above conditions is found, the processor 104 may directly define this pixel as the reference point pixel 312 corresponding to the left flap of the mitral valve and stop the scanning process.

With reference to FIG. 5C, which is a schematic view illustrating finding of a reference point pixel corresponding to a right flap of the mitral valve according to FIG. 5B. In the case that the heart ultrasound image 30 is determined to be the apical view, among the 3 found reference point pixels, the lower right one should correspond to the right flap of the mitral valve.

Accordingly, starting from the lowest pixel row in the left ventricular mask image 31, the processor 104 may scan from right to left row by row to find the pixel satisfying the above conditions (e.g., the pixel having 8 surrounding pixels including 3 first surrounding pixels with the first value and 5 second surrounding pixels with the second value and having the first value).

In FIG. 5A, when one pixel satisfying the above conditions is found, the processor 104 may determine whether this pixel has been defined as another reference point pixel (e.g., the reference point pixel 312) first. If no is determined, the processor 104 may directly define this pixel as the reference point pixel 313 corresponding to the right flap of the mitral valve and stop the scanning process. In contrast, if this pixel has been defined as another reference point pixel (e.g., the reference point pixel 312), the processor 104 may ignore this pixel first and continues to scan upwards to find another pixel satisfying the above conditions. When another pixel satisfying the above conditions is found, the processor 104 may directly define the another pixel as the reference point pixel 313 corresponding to the right flap of the mitral valve and stop the scanning process.

In other embodiments, other manners, in addition to the manners shown in FIG. 5A to FIG. 5C, may also be adopted by the processor 104 to find the reference point pixels 311 to 313 in the left ventricular mask image 31.

Based on the above, it can be seen that in the method for estimating the ventricular volume provided by the disclosure, after the left ventricular mask image corresponding to left ventricular ultrasound is obtained, 3 pixels satisfying specific conditions (e.g., the pixel having 8 surrounding pixels including 3 first surrounding pixels with the first value and 5 second surrounding pixels with the second value and having the first value) are found to act as the reference point pixels corresponding to the apex and the two flaps of the mitral valve. Thereafter, the left ventricular volume may be estimated based on the reference point pixels. In this way, in the disclosure, the left ventricular volume may be effectively and automatically estimated without the need to manually mark the apex and the flaps on both sides of the mitral valve.

In other embodiments, the disclosure provides a method for evaluating a movement state of a heart capable of determining whether an abnormal movement state of the heart occurs based on a change in the left ventricular volume. In the embodiments of the disclosure, the processor 104 may access the modules and program codes in the storage circuit 102 to implement the method for evaluating the movement state of the heart provided by the disclosure, and detailed description is provided as follows.

Figure 6:
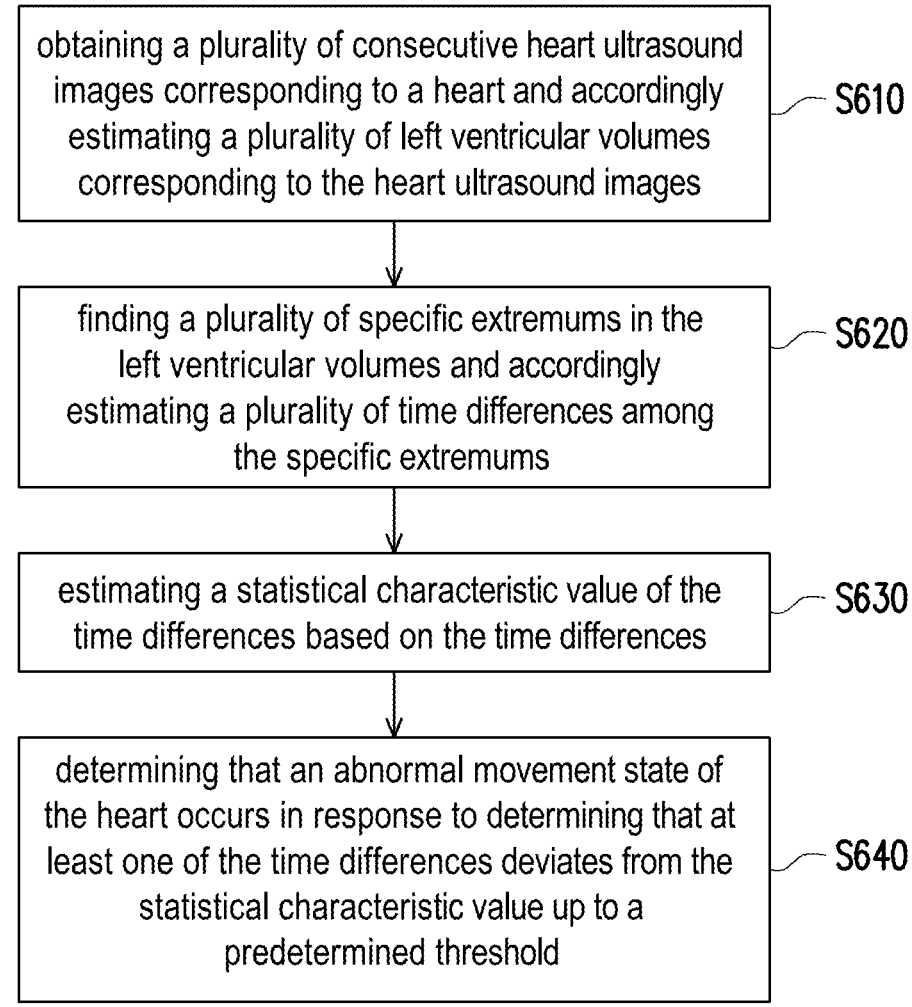
FIG. 6 is a flow chart illustrating a method for evaluating a movement state of a heart according to an embodiment of the disclosure.

With reference to FIG. 6, which is a flow chart illustrating a method for evaluating a movement state of a heart according to an embodiment of the disclosure. The method provided by this embodiment may be executed by the electronic apparatus 100 in FIG. 1, and each step in FIG. 6 is described in detail together with the devices shown in FIG. 1.

First, in step S610, the processor 104 may obtain a plurality of consecutive heart ultrasound images corresponding to a heart (e.g., a heart of a specific patient) and accordingly estimate a plurality of left ventricular volumes corresponding to the heart ultrasound images.

In an embodiment, the processor 104 may obtain the heart ultrasound images first and determine whether each of the heart ultrasound images belongs to the apical view (e.g., A2C or A4C). In an embodiment, the processor 104 may determine whether each of the heart ultrasound images belongs to the apical view based on, for example, the technique recorded in the document "Guidelines for Performing a Comprehensive Transthoracic Echocardiographic Examination in Adults: Recommendations from the American Society of Echocardiography". Since related details may be found with reference to the above document, description thereof is not repeated herein.

In response to determining that each of the heart ultrasound images belongs to the apical view, the processor 104 may retrieve a left ventricular mask image corresponding to a left ventricle of the heart from each of the heart ultrasound images and accordingly estimate a left ventricular volume corresponding to each of the heart ultrasound images.

In an embodiment, the processor 104 may, for example, input each of the heart ultrasound images into the above-mentioned machine learning model, and the machine learning model may output the corresponding left ventricular mask image corresponding to each of the heart ultrasound images.

In the embodiments of the disclosure, regarding each of the left ventricular mask images, the processor 104 may estimate the corresponding left ventricular volume based on the mechanisms taught in FIG. 2 to FIG. 5C, so detailed description is not repeated herein.

Figure 7A:
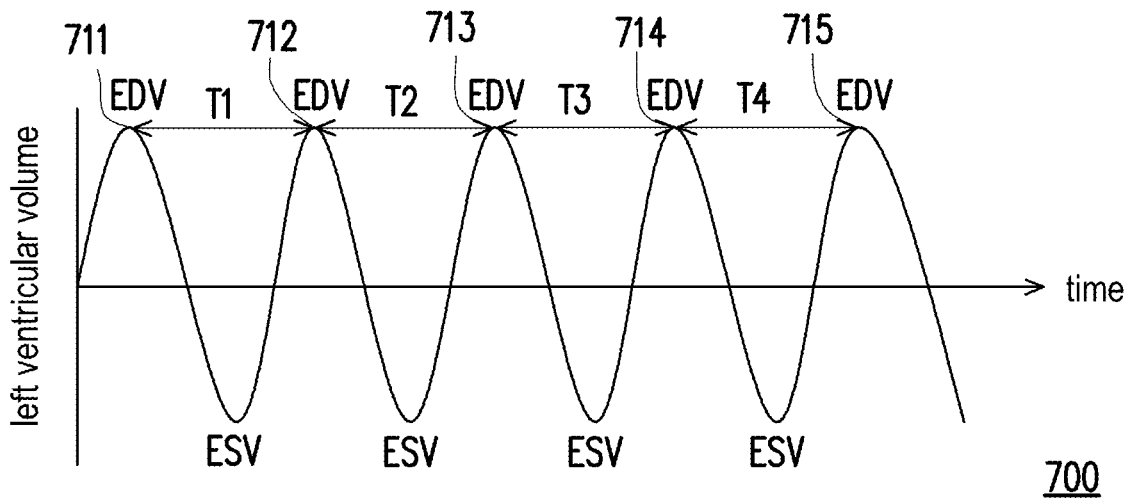
FIG. 7A is a view illustrating an application scenario according to an embodiment of the disclosure.

In order to facilitate the description of the concept of the disclosure, the following may be supplemented with FIG. 7A for further description, and FIG. 7A is a view illustrating an application scenario according to an embodiment of the disclosure. In FIG. 7A, a plurality of consecutive left ventricular volumes obtained in step S610 may be depicted as a left ventricular volume change graph 700 shown in FIG. 7A.

Next, in step S620, the processor 104 may find a plurality of specific extremums 711 to 715 in the left ventricular volumes and accordingly estimate a plurality of time differences T1 to T4 among the specific extremums 711 to 715.

In an embodiment, the processor 104 may treat, but not limited to, a plurality of specific left ventricular volumes corresponding to end-diastolic volumes (EDVs) s among the left ventricular volumes as the specific extremums, for example. By definition, each EDV should correspond to the largest left ventricular volume in a heart rate cycle to which it belongs. Based on this, if the processor 104 determines that an $i^{th}$ (i is an integer) left ventricular volume among the left ventricular volumes is greater than an $i-1^{th}$ left ventricular volume and an $i+i^{th}$ left ventricular volume, the processor 104 may then determine that the $i^{th}$ left ventricular volume should correspond to the EDV and may further determine that the $i^{th}$ left ventricular volume belongs to one of the specific extremums.

In the scenario in FIG. 7A, since the left ventricular volume change graph 700 may be understood has including 5 heart rate cycles, the processor 104 may find 5 EDVs as the specific extremums 711 to 715 according to the above principle. Next, the processor 104 may then estimate the time differences T1 to T4 among the specific extremums 711 to 715.

Roughly speaking, it is assumed that the specific extremums found by the processor 104 include a $1^{st}$ specific extremum to a $K^{th}$ (where K is an integer) specific extremum, and a time difference between a $i^{th}$ specific extremum and a $i^{th}$ specific extremum may be defined as a $i^{th}$ time difference, where $1 \leq j \leq K-1$.

Taking FIG. 7A as an example, the time difference T1 (may be understood as a $1^{st}$ time difference) is, for example, the time difference between the specific extremum 711 (may be understood as the $1^{st}$ specific extremum) and the specific extremum 712 (may be understood as a $2^{nd}$ specific extremum). The time difference T2 (may be understood as a $2^{nd}$ time difference) is, for example, the time difference between the specific extremum 712 (may be understood as the $2^{nd}$ specific extremum) and the specific extremum 713 (may be understood as a $3^{rd}$ specific extremum). The time difference T3 (may be understood as a 3-nd time difference) is, for example, the time difference between the specific extremum 713 (may be understood as the $3^{rd}$ specific extremum) and the specific extremum 714 (may be understood as a $4^{th}$ specific extremum). The time difference T4 (may be understood as a $4^{th}$ time difference) is, for example, the time difference between the specific extremum 714 (may be understood as the $4^{th}$ specific extremum) and the specific extremum 715 (may be understood as a $5^{th}$ specific extremum), which should however not be construed as limitations to the disclosure.

After that, in step S630, the processor 104 may estimate a statistical characteristic value (including but not limited to an average value of the time differences T1 to T4) of the time differences T1 to T4 based on the time differences T1 to T4. Further, the processor 104 may determine whether each of the time differences T1 to T4 deviates from the statistical characteristic value up to a predetermined threshold. In different embodiments, the predetermined threshold may be set to any ratio value according to a designer's needs, such as, but not limited to, 5%.

In step S640, in response to determining that at least one of the time differences T1 to T4 deviates from the statistical characteristic value up to the predetermined threshold, the processor 104 may determine that the abnormal movement state (e.g., an arrhythmia state) of the heart occurs. In contrast, in response to determining that all of the time differences T1 to T4 do not deviate from the statistical characteristic value up to the predetermined threshold, the processor 104 may determine that the abnormal movement state of the heart does not occur.

In FIG. 7A, it is assumed that if the processor 104 determines that all of the time differences T1 to T4 do not deviate from the statistical characteristic value up to the predetermined threshold, the processor 104 may then determine that the abnormal movement state of the heart, such as the arrhythmia state and the like, does not occur.

Figure 7B:
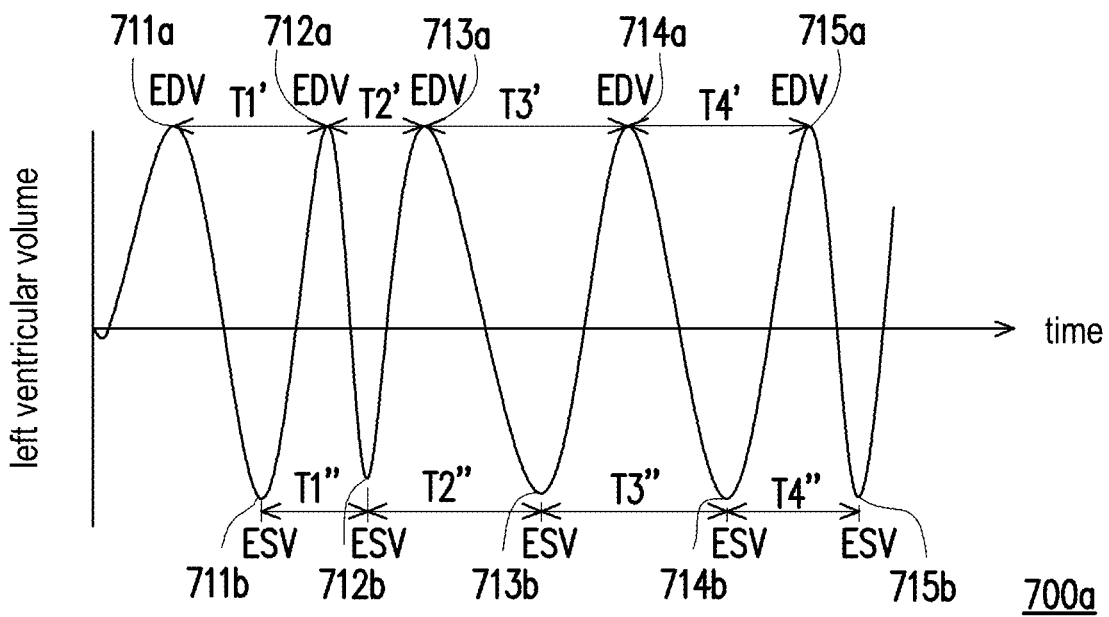
FIG. 7B is a view illustrating another application scenario according to FIG. 7A.

With reference to FIG. 7B, which is a view illustrating another application scenario according to FIG. 7A. In this embodiment, it is assumed that the processor 104 obtains a left ventricular volume change graph 700a as shown in FIG. 7B according to the above teachings and finds a plurality of specific extremums 711a to 715a corresponding to the EDVs and corresponding time differences T1' to T4'.

In FIG. 7B, it is assumed that the processor 104 determines that the time difference T2' among the time differences T1' to T4' deviates from a statistical characteristic value of the time differences T1' to T4' up to a predetermined threshold, the processor 104 may then determine that the abnormal movement state (e.g., the arrhythmia state) of the heart occurs, which should however not be construed as limitations to the disclosure.

In the embodiments of the disclosure, the processor 104 may provide the relevant medical personnel with, but not limited to, the determination result of whether the abnormal movement state of the heart occurs, as a reference for diagnosis.

In addition, although the left ventricular volumes corresponding to the EDVs are used as the considered specific extreme values in the above embodiments, in other embodiments, the processor 104 may also use the left ventricular volumes corresponding to end-systolic volumes (ESVs) as the considered specific extreme values. By definition, each ESV should correspond to the smallest left ventricular volume in the heart rate cycle to which it belongs. Based on this, if the processor 104 determines that the $i^{th}$ left ventricular volume among the left ventricular volumes is less than the $i-1^{th}$ left ventricular volume and the $i+1^{th}$ left ventricular volume, the processor 104 may then determine that the $i^{th}$ left ventricular volume should correspond to the ESV and may further determine that the $i^{th}$ left ventricular volume belongs to one of the specific extremums.

Based on this, in the scenario shown in FIG. 7B, the processor 104 may correspondingly find the left ventricular volumes corresponding to the ESVs to act as specific extremums 711b to 715b and accordingly estimate corresponding time differences T1" to T4".

In FIG. 7B, it is assumed that the processor 104 determines that the time difference T1" among the time differences T1" to T4" deviates from a statistical characteristic value of the time differences T1" to T4" up to a predetermined threshold, the processor 104 may then determine that the abnormal movement state (e.g., the arrhythmia state) of the heart occurs, which may be used as a reference for diagnosis for related medical personnel.

In some embodiments, if the relevant medical personnel determines that the abnormal movement state of the heart is misjudged as occurring after examining the heart ultrasound image corresponding to FIG. 7B (that is, the abnormal movement state of the heart does not actually occurs), the relevant medical personnel may report this situation to the electronic apparatus 100.

In the embodiments of the disclosure, since the above misjudgment may be caused by an unfavorable recognition ability of the machine learning model for the left ventricular image region, the processor 104 may retrain the machine learning model accordingly to reduce the probability of misjudgment in the future, which should however not be construed as limitations to the disclosure.

In view of the foregoing, in the method for estimating the ventricular volume provided by the disclosure, after the left ventricular mask image corresponding to left ventricular ultrasound is obtained, 3 pixels satisfying the specific conditions are found to act as the reference point pixels corresponding to the apex and the two flaps of the mitral valve. Thereafter, the left ventricular volume may be estimated based on the reference point pixels. In this way, in the disclosure, the left ventricular volume may be effectively and automatically estimated without the need to manually mark the apex and the flaps on both sides of the mitral valve.

In addition, in the method for evaluating the movement state of the heart provided by the disclosure, the specific extremums corresponding to the EDVs (or ESVs) may be found in the left ventricular volumes of the consecutive heart ultrasound images, and whether the abnormal movement state of the heart such as arrhythmia occurs may be determined based on the time differences among the specific extremums. In this way, relevant medical personnel may easily learn the condition of the heart, and the probability of making incorrect assessments (for example, incorrect ejection fraction is calculated, etc.) is therefore lowered.

It will be apparent to those skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. A method for evaluating a movement state of a heart, suitable for an electronic apparatus, the method comprising:
obtaining a plurality of consecutive heart ultrasound images corresponding to the heart and accordingly estimating a plurality of left ventricular volumes corresponding to the plurality of consecutive heart ultrasound images, comprising:
obtaining the plurality of consecutive heart ultrasound images and determining whether each of the plurality of consecutive heart ultrasound images belongs to an apical view;
in response to determining that each of the plurality of consecutive heart ultrasound images belongs to the apical view, retrieving a left ventricular mask image corresponding to a left ventricle of the heart from each of the plurality of consecutive heart ultrasound images, wherein the left ventricular mask image is a binary image; and
estimating a left ventricular volume corresponding to each of the plurality of consecutive heart ultrasound images according to the left ventricular mask image of each of the plurality of consecutive heart ultrasound images, comprising:
finding 3 reference point pixels in the left ventricular mask image of each of the plurality of consecutive heart ultrasound images, wherein each of the reference point pixels has a first value, each of the reference point pixels is surrounded by N surrounding pixels, and the surrounding pixels of each of the reference point pixels comprise N1 first surrounding pixels with the first value and N2 second surrounding pixels with a second value, wherein N, N1, and N2 are positive integers; and
estimating the left ventricular volume corresponding to each of the plurality of consecutive heart ultrasound images based on the reference point pixels in the left ventricular mask image of each of the plurality of consecutive heart ultrasound images;
finding a plurality of specific extremums in the plurality of left ventricular volumes and accordingly estimating a plurality of time differences among the plurality of specific extremums;
estimating a statistical characteristic value of the plurality of time differences based on the plurality of time differences; and
determining that an abnormal movement state of the heart occurs in response to determining that at least one of the plurality of time differences deviates from the statistical characteristic value up to a predetermined threshold.

2. The method according to claim 1, wherein the step of retrieving the left ventricular mask image corresponding to the left ventricle of the heart from each of the plurality of consecutive heart ultrasound images comprises:
inputting each of the plurality of consecutive heart ultrasound images into a machine learning model, wherein the machine learning model outputs the corresponding left ventricular mask image in response to each of the plurality of consecutive heart ultrasound images.

3. The method according to claim 2, further comprising:
retraining the machine learning model in response to determining that the abnormal movement state of the heart is misjudged as occurring.

4. The method according to claim 1, wherein the step of finding the plurality of specific extremums in the plurality of left ventricular volumes comprises:

determining that an ith left ventricular volume belongs to one of the plurality of specific extremums in response to determining that the ith left ventricular volume among the plurality of left ventricular volumes is greater than an i−1th left ventricular volume and an i+1th left ventricular volume, wherein i is an integer.

5. The method according to claim 1, wherein the step of finding the plurality of specific extremums in the plurality of left ventricular volumes comprises:

determining that an ith left ventricular volume belongs to one of the plurality of specific extremums in response to determining that the ith left ventricular volume among the plurality of left ventricular volumes is less than an i−1th left ventricular volume and an i+1th left ventricular volume.

6. The method according to claim 1, wherein the plurality of specific extremums comprise a 1st specific extremum to a Kth specific extremum, and the plurality of time differences comprise a 1st time difference to a K−1th time difference, wherein a jth time difference among the plurality of time differences is a time difference between a j+1th specific extremum and a jth specific extremum, and $1 \leq j \leq K-1$, wherein K is an integer.

7. The method according to claim 1, wherein the statistical characteristic value is an average value of the plurality of time differences.

8. The method according to claim 1, wherein the abnormal movement state comprises an arrhythmia state.

* * * * *